United States Patent
Zuk et al.

(10) Patent No.: US 10,718,764 B2
(45) Date of Patent: Jul. 21, 2020

(54) ELECTROCHEMILUMINESCENT DETECTION SYSTEM

(71) Applicant: Access Medical Systems, LTD., Palo Alto, CA (US)

(72) Inventors: Robert F. Zuk, Menlo Park, CA (US); Hong Tan, San Jose, CA (US)

(73) Assignee: Access Medical Systems, LTD., Palo Alto, CA (US)

( * ) Notice: Subject to any disclaimer, the term of this patent is extended or adjusted under 35 U.S.C. 154(b) by 460 days.

(21) Appl. No.: 15/255,558

(22) Filed: Sep. 2, 2016

(65) Prior Publication Data

US 2017/0052178 A1 Feb. 23, 2017

Related U.S. Application Data

(63) Continuation of application No. 14/165,381, filed on Jan. 27, 2014, now Pat. No. 9,435,794, which is a continuation of application No. 13/676,970, filed on Nov. 14, 2012, now Pat. No. 8,647,889, which is a continuation of application No. PCT/US2012/033808, filed on Apr. 16, 2012.

(60) Provisional application No. 61/477,171, filed on Apr. 20, 2011.

(51) Int. Cl.
| | |
|---|---|
| G01N 33/543 | (2006.01) |
| G01N 33/533 | (2006.01) |
| G01N 33/53 | (2006.01) |
| G01N 21/76 | (2006.01) |
| G01N 27/327 | (2006.01) |
| G01N 33/553 | (2006.01) |
| G01N 21/75 | (2006.01) |

(52) U.S. Cl.
CPC ....... *G01N 33/54393* (2013.01); *G01N 21/76* (2013.01); *G01N 27/3277* (2013.01); *G01N 33/533* (2013.01); *G01N 33/5306* (2013.01); *G01N 33/5438* (2013.01); *G01N 33/553* (2013.01); *G01N 2021/757* (2013.01)

(58) Field of Classification Search
CPC ........... G01N 33/533; G01N 33/54393; G01N 27/3277; G01N 21/76; G01N 2021/757
See application file for complete search history.

(56) References Cited

U.S. PATENT DOCUMENTS

| | | |
|---|---|---|
| 3,996,345 A | 12/1976 | Ullman et al. |
| 4,169,137 A | 9/1979 | Hirschfeld et al. |
| 4,200,613 A | 4/1980 | Alfrey et al. |
| 4,208,479 A | 6/1980 | Zuk et al. |
| 4,272,510 A | 6/1981 | Smith et al. |
| 4,276,259 A | 6/1981 | Eibl et al. |
| 4,299,916 A | 11/1981 | Litman et al. |
| 4,434,150 A | 2/1984 | Azad et al. |
| 4,447,546 A | 5/1984 | Hirschfeld |
| 4,483,925 A | 11/1984 | Noack |
| 4,599,315 A | 7/1986 | Terasaki et al. |
| 4,608,344 A | 8/1986 | Carter et al. |
| 4,704,353 A | 11/1987 | Humphries et al. |
| 4,778,751 A | 10/1988 | El Shami et al. |
| 4,780,423 A * | 10/1988 | Bluestein ......... G01N 33/54313 436/527 |
| 4,822,565 A | 4/1989 | Kohler |
| 4,882,269 A | 11/1989 | Schneider et al. |
| 4,891,321 A | 1/1990 | Hubscher |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,320,814 A | 6/1994 | Walt et al. |
| 5,449,625 A | 9/1995 | Kobayashi et al. |
| 5,486,616 A | 1/1996 | Waggoner et al. |
| 5,494,830 A | 2/1996 | Hubscher |

(Continued)

FOREIGN PATENT DOCUMENTS

| | | |
|---|---|---|
| CN | 2567573 Y | 8/2003 |
| CN | 1553188 A | 12/2004 |

(Continued)

OTHER PUBLICATIONS

Blackburn, Gary F. et al.: "Electrochemiluminescence Detection for Development of Immunoassays and DNA Probe Assays for Clinical Diagnostics", Clinical Chemistry, American Association for Clinical Chemistry, Washington, DC, vol. 37, No. 9, Sep. 1, 1991, pp. 1534-1539.

European Search Report for Application No. 12773652.8, dated Mar. 30, 2015.

Extended European Search Report dated Jul. 30, 2012 for Application No. EP10749212.

International Search Report and Written Opinion for International App. No. PCT/US2012/033808 dated Oct. 16, 2012.

(Continued)

*Primary Examiner* — Ann Y Lam
(74) *Attorney, Agent, or Firm* — Perkins Coie LLP; Viola T. Kung (57) ABSTRACT

The present invention is directed to a luminescent immunoassay method for detecting an analyte in a liquid sample with high sensitivity. The invention provides a unique combination of (i) using a probe having a small sensing surface area for binding analyte molecules, (ii) using a high molecular weight branched polymer conjugated with multiple binding molecules and multiple luminescent labels, and (iii) cycling the probe having immunocomplex formed back to the reagent vessel and amplification vessel 1-10 times and repeating the reaction with the reagent and the amplification polymer, to improve the sensitivity of detection level. For each cycling, the luminescent signal is increased significantly over the noise. The present invention is also directed to an electrochemiluminescent detection system for measuring a chemiluminescent signal on a probe tip.

7 Claims, 5 Drawing Sheets

(56) References Cited

U.S. PATENT DOCUMENTS

| | | | |
|---|---|---|---|
| 5,650,334 | A | 7/1997 | Zuk et al. |
| 5,814,524 | A | 9/1998 | Walt et al. |
| 5,993,740 | A * | 11/1999 | Niiyama .......... G01N 33/54326 209/215 |
| 6,146,593 | A | 11/2000 | Pinkel et al. |
| 6,197,597 | B1 | 3/2001 | Tuunanen |
| 6,210,910 | B1 | 4/2001 | Walt et al. |
| 6,225,047 | B1 | 5/2001 | Hutchens et al. |
| 6,277,628 | B1 | 8/2001 | Johann et al. |
| 6,399,397 | B1 | 6/2002 | Zarling et al. |
| 6,667,159 | B1 | 12/2003 | Walt et al. |
| 6,878,539 | B1 * | 4/2005 | Fritzsche ............ G01N 33/5438 435/285.2 |
| 7,651,869 | B2 | 1/2010 | Saaski et al. |
| 7,713,751 | B2 | 5/2010 | Nikitin et al. |
| 7,927,789 | B1 | 4/2011 | Baird et al. |
| 8,309,369 | B2 | 11/2012 | Tan et al. |
| 8,492,139 | B2 * | 7/2013 | Tan ...................... G01N 21/645 435/288.7 |
| 8,859,297 | B2 * | 10/2014 | Alocilja ................. B82Y 15/00 436/523 |
| 10,379,116 | B2 * | 8/2019 | Tan .................. G01N 33/54373 |
| 2002/0123078 | A1 * | 9/2002 | Seul ..................... B01J 19/0046 435/7.2 |
| 2002/0142340 | A1 | 10/2002 | Waggoner |
| 2003/0124595 | A1 | 7/2003 | Lizardi |
| 2004/0189311 | A1 * | 9/2004 | Glezer ................. B01L 3/5027 324/444 |
| 2005/0095646 | A1 * | 5/2005 | Sherman .......... G01N 33/54306 435/7.1 |
| 2006/0127942 | A1 | 6/2006 | Straume et al. |
| 2007/0034529 | A1 | 2/2007 | Bard et al. |
| 2007/0105176 | A1 | 5/2007 | Ibey et al. |
| 2007/0298006 | A1 | 12/2007 | Tomalia et al. |
| 2009/0017197 | A1 * | 1/2009 | Zhang ................ G01N 33/5438 427/126.5 |
| 2009/0123939 | A1 * | 5/2009 | Alocilja ............ G01N 27/745 435/7.2 |
| 2010/0006451 | A1 * | 1/2010 | Gordon .............. G01N 33/5438 205/777.5 |
| 2010/0062544 | A1 | 3/2010 | Evans et al. |
| 2011/0312105 | A1 * | 12/2011 | Tan ...................... G01N 21/645 436/501 |

FOREIGN PATENT DOCUMENTS

| | | |
|---|---|---|
| EP | 0522677 A1 | 1/1993 |
| WO | 1992008979 A1 | 5/1992 |
| WO | 2009126249 A1 | 10/2009 |
| WO | 2010101931 A2 | 9/2010 |

OTHER PUBLICATIONS

Wang, "MEMS Design and Manufacturing," Tsinghua University Ed. (Feb. 19, 2008) 3 pages.

* cited by examiner

ELECTROCHEMILUMINESCENT DETECTION SYSTEM

This application is a continuation of U.S. application Ser. No. 14/165,381, filed Jan. 27, 2014; which is a continuation of U.S. application Ser. No. 13/676,970, filed Nov. 14, 2012, now U.S. Pat. No. 8,647,889; which is a continuation of PCT/US2012/033808, filed Apr. 16, 2012; which claims the priority of U.S. Provisional Application No. 61/477,171, filed Apr. 20, 2011. The contents of the above-identified applications are incorporated herein by reference in their entireties.

FIELD OF THE INVENTION

The invention relates to a method for detecting an analyte in a liquid sample using a probe having a small surface and a branched polymer having multiple binding molecules and multiple fluorescent or chemiluminescent labels. The sensitivity of the method is improved by cycling the binding reaction and amplification reaction several times.

BACKGROUND OF THE INVENTION

In many immunoassays applications it is desirable to develop high sensitivity detection methods. Luminescent dyes, emitting either fluorescent or chemiluminescent signals, offer several practical advantages, i.e. stability, low cost, amenable to labeling procedures and spectral properties with minimal interference from biological samples or solid phase substrates. Fluorescent dyes have a disadvantage compared to other detection methods, particularly ELISA, where enzyme activity amplifies the amount of detectable signal associated with immune complex formation.

Arylsulfonate cyanine fluorescent dyes are described in Mujumdar et al. (1993) *Bioconjugate Chemistry*, 4:105-111; Southwick et al. (1990) *Cytometry*, 11:418-430; and U.S. Pat. No. 5,268,486. Cy5 is described in each of the references and is commercially available from Biological Detection Systems, Inc., Pittsburgh, Pa., under the tradename FLUOROLINK™ Cy5™. The arylsulfonate cyanine fluorescent dyes have high extinction coefficients (typically from 130,000 L/mole to 250,000 L/mole), good quantum yields, fluorescent emission spectra in a range (500 nm to 750 nm) outside of the autofluorescence wavelengths of most biological materials and plastics, good solubilities, and low non-specific binding characteristics.

Despite these excellent properties, arylsulfonate cyanine fluorescent dyes suffer from certain limitations. In particular, these dyes have a relatively narrow Stokes shift which results in significant overlap between the excitation and emission spectra of the dye. The overlap of excitation and emission spectra, in turn, can cause self-quenching of the fluorescence when the dye molecules are located close to each other when excited. Such self-quenching limits the number of arylsulfonate dye molecules which can be conjugated to a single antibody molecule for use in immunoassays. In the case of Cy5, an exemplary arylsulfonate cyanine fluorescent dye, the Stokes shift is 17 nm (which is the difference between an excitation wavelength of 650 nm and an emission wavelength of 667 nm). Optimal fluorescent yield is obtained when from two to four Cy5 molecules are conjugated to a single antibody molecule. The fluorescent signal output drops rapidly when more than four dye molecules are conjugated to a single antibody molecule. The inability to conjugate more than four dye molecules to individual antibody molecules significantly limits the sensitivity of immunoassays using Cy5-labelled antibodies and other binding substances.

U.S. Publication 2011/0312105 discloses a detection system and fluorescent immunoassays; the publication is incorporated herein by reference in its entirety. This publication does not disclose amplification by cycling the probe back and forth in the reagent vessel and the amplification vessel.

There is a need for an improved method for detecting analytes with high sensitivity by fluorescent or chemiluminescent immunoassay. The method should be easy to handle by the users and should provide high specific signal and minimal background noise.

SUMMARY OF INVENTION

The present invention is directed to a luminescent immunoassay method for detecting an analyte in a liquid sample with high sensitivity. The method comprises the steps of: (a) obtaining a probe having a first antibody immobilized on the tip of the probe; (b) dipping the probe tip into a sample vessel containing a sample solution having an analyte to bind the analyte to the first antibody on the probe tip; (c) dipping the probe tip into a reagent vessel containing a reagent solution comprising a reagent of a second antibody conjugated with a first member of a binding pair to bind the reagent to the analyte; (d) dipping the probe tip into a washing vessel containing a wash solution to wash the probe tip; (e) dipping the probe tip into an amplification vessel containing an amplification solution comprising a polymer conjugated with at least 5 molecules of second member of the binding pair and at least 25 luminescent labels, to form an immunocomplex of the analyte, the first antibody, the second antibody, and the first and the second members of the binding pair on the probe tip, wherein the polymer is branched and has a molecular weight of at least 1 million daltons, and the luminescent labels has a molecular weight of less than 2,000 Daltons; (f) dipping the probe tip into a washing vessel containing a wash solution to wash the probe tip; (g) repeating steps (c) to (f) 1-10 times, and (g) detecting the immunocomplex formed by measuring the luminescent signal on the probe tip.

The present invention is also directed to a composition comprising (a) a branched polymer having a molecular weight of at least 1 million Daltons, (b) at least 5 binding molecules, and (c) at least 25 chemiluminescent molecules selected from the group consisting of ruthenium(II)trisbipyridine, luminol, acridinium ester, and hemin; wherein the binding molecules and the chemiluminescent molecules are attached to the polymer.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within ±10% of the recited value.

An "analyte-binding molecule", as used herein, refers to any molecule capable of participating in a specific binding reaction with an analyte molecule.

An "aspect ratio" of a shape refers to the ratio of its longer dimension to its shorter dimension.

A "binding molecule," refers to a molecule that is capable to bind another molecule of interest.

A "binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, biotin and neutravidin (a deglycosylated version of avidin), lectin and carbohydrates. Preferred binding pairs are biotin and streptavidin, biotin and avidin, biotin and neutravidin, fluorescein and anti-fluorescein, digioxigenin/anti-digioxigenin, DNP (dinitrophenol)/anti-DNP.

A "branched polymer," as used herein, refers to a non-linear polymer having a 2- or 3-dimensional structure, which can be either a naturally occurring branched polymer, or a synthetically crosslinked polymer.

"Chemiluminescence," as used herein, refers to the emission of energy with limited emission of luminescence, as the result of a chemical reaction. For example, when luminol reacts with hydrogen peroxide in the presence of a suitable catalyst, it produces 3-aminophthalate in an excited state, which emits light when it decays to a lower energy level.

A "dendrimer," as used herein, refers to repetitively organic, branched molecules. A dendrimer is typically symmetric around the core, and often adopts a spherical three-dimensional morphology.

"Electrochemiluminescence," (ECL), as used herein, refers to luminescence produced during electrochemical reactions in solutions. In ECL, electrochemically generated intermediates undergo a highly exergonic reaction to produce an electronically excited state and then emits light. ECL excitation is caused by energetic electron transfer (redox) reactions of electrogenerated species. ECL is usually observed during application of potential (several volts) to electrodes of electrochemical cell that contains solution of luminescent species.

"Immobilized," as used herein, refers to reagents being fixed to a solid surface. When a reagent is immobilized to a solid surface, it is either be non-covalently bound or covalently bound to the surface.

A "monolithic substrate," as used herein, refers to a single piece of a solid material.

A "probe," as used herein, refers to a substrate coated with a thin-film layer of analyte-binding molecules at the sensing side. A probe has a distal end and a proximal end. The proximal end (also refers to probe tip in the application) has a sensing surface coated with a thin layer of analyte-binding molecules.

High Sensitivity Luminescent Immunoassay

The present invention is directed to a high sensitivity immunoassay method. The inventors have discovered that the unique combination of (i) using a probe having a small sensing surface area for binding analyte molecules, (ii) using a high molecular weight branched polymer conjugated with multiple binding molecules and multiple luminescent labels, and (iii) cycling the probe having immunocomplex formed back to the reagent vessel and amplification vessel 1-10 times and repeating the reaction with the reagent and the amplification polymer, improves the sensitivity of detection level. For each cycling, the luminescent signal is increased significantly over the noise.

The present method offers high sensitivity and precision without increasing the overall complexity of the assay reagents, consumable and instrumentation. The method entails the transfer of a probe back and forth between two reagents one of which is an amplification polymer labeled with multiple binding molecules and multiple luminescent labels. The polymer has a molecular weight of ≥400K, preferably ≥1 million Dalton. Crosslinking of the polymer is desirable to control the molecular size distribution and non-specific binding. The polymer should carrier at the minimum 5 binding molecules per polymer, preferably more than 10. Luminescent labels should be small with a molecular weight of <5K Dalton. The inventors have discovered that simply cycling the reactions without using the polymer as described above in the amplification does not improve the sensitivity.

The present method detects an analyte in a liquid sample. The method comprises the steps of: (a) obtaining a probe having a first antibody immobilized on the tip of the probe, wherein the diameter of the tip surface is ≤5 mm; (b) dipping the probe tip into a sample vessel containing a sample solution having an analyte to bind the analyte to the first antibody on the probe tip; (c) dipping the probe tip into a reagent vessel containing a reagent solution comprising a reagent of a second antibody conjugated with a first member of a binding pair to bind the reagent to the analyte; (d) dipping the probe tip into a first wash vessel containing a wash solution to wash the probe tip; (e) dipping the probe tip into an amplification vessel containing an amplification solution comprising a polymer conjugated with at least 5 molecules of second member of the binding pair and at least 25 luminescent labels, to form an immunocomplex of the analyte, the first antibody, the second antibody, and the first and the second members of the binding pair on the probe tip, wherein the polymer is branched, and has a molecular weight of at least 1 million daltons, and the luminescent labels has a molecular weight of less than 2,000 Daltons; (f) dipping the probe tip into a second wash vessel containing a wash solution to wash the probe tip; (g) repeating steps (c) to (f) 1-10 times, and (h) detecting the immunocomplex formed by measuring the luminescent signal on the probe tip; wherein the first antibody and the second antibody are antibodies against the analyte.

In step (a), the probe can be any shape such as rod, cylindrical, round, square, triangle, etc., with an aspect ratio of length to width of at least 5 to 1, preferably 10 to 1. A rod-shape is preferred. Because the probe is dipped in a sample solution and one or more assay solutions during an immunoassay, it is desirable to have a long probe with an aspect ratio of at least 5 to 1 to enable the probe tip's immersion into the solutions. For fluorescent assay, the probe can be a monolithic substrate.

The probe has a small tip for binding analytes. The tip has a smaller surface area with a diameter ≤5 mm, preferably ≤2 mm or ≤1 mm, e.g., 0.5-2 mm. The small surface of the probe tip provides several advantages. First, a small surface has less non-specific binding and thus produces a lower background signal. Second, the reagent or sample carry over on the probe tip is extremely small due to the small surface area of the tip. This feature makes the probe tip easy to wash, and causes negligible contamination in the wash solution since the wash solution has a larger volume. Further, small surface area of the probe tip has a small binding capacity. Consequently, when the probe tip is immersed in a reagent solution, the binding of the reagent does not consume a significant amount of the reagent. The reagent concentration is effectively unchanged. Negligible contamination of the wash solution and small consumption of the reagents enable the reagent solution, the amplification solution, and the wash solution to be re-used many times, for example, 1-10 times.

The sensing surface of the probe is coated with first antibody which binds to the analyte in a sample. Methods to immobilize reagents to the solid phase (the sensing surface of the probe tip) are common in immunochemistry and involve formation of covalent, hydrophobic or electrostatic bonds between the solid phase and reagent. The first antibody can be directly immobilized on the sensing surface. Alternatively, the first antibody can be indirectly immobilized on the sensing surface through a binding pair. For example, anti-fluorescein can be first immobilized either by adsorption to the solid surface or by covalently binding to aminopropylsilane coated on the solid surface. Then the first antibody that is labeled with fluorescein can be bound to the solid surface through the binding of fluorescein and anti-fluorescein (binding pair).

In step (b), the probe tip is dipped into a sample vessel for 20 seconds to 60 minutes, preferably 20 seconds to 10 minutes, to bind the analyte to the first antibody on the probe tip.

After step (b), the probe is optionally washed 1-5 times, preferably 1-3 times in a wash vessel containing a wash solution. This extra washing step may not be required because the amount of the carried-over solution is minimal due to a small binding surface area. The wash solution typically contains buffer and a surfactant such as Tween 20.

In step (c), the probe tip is dipped into a reagent vessel for 20 seconds to 10 minutes, preferably 20 seconds to 2 minutes to bind the reagent to the analyte on the probe tip. The reagent solution comprises a reagent of a second antibody conjugated with a first member of a binding pair.

The binding pair is typically a hapten and its antibody, a ligand and its receptor, complementary strands of nucleic acids, or lectin and carbohydrates. For example, the binding pair is biotin and streptavidin, biotin and avidin, biotin and neutravidin, fluorescein and anti-fluorescein, digioxigenin and anti-digioxigenin, and DNP (dinitrophenol) and anti-DNP. Preferably, the first member of the binding pair is biotin and the second member of the binding pair is streptavidin.

In Step (d), the probe is washed 1-5 times, preferably 1-3 times in a wash vessel containing a wash solution. The wash solution typically contains buffer and a surfactant such as Tween 20.

In step (e), the probe is dipped into an amplification vessel containing an amplification solution for 20 seconds to 5 minutes, preferably 20 seconds to 2 minutes, to form an immunocomplex of the analyte, the first antibody, the second antibody, and the first and the second members of the binding pair on the probe tip. The amplification solution comprises a polymer conjugated with at least 5 molecules of second member of the binding pair and at least 25 luminescent labels. The polymer is branched, and has a molecular weight of at least 500,000, preferably 1 million Daltons. The polymer can be a polysaccharide (e.g. FICOLL® or dextran), a polynucleotide, a dendrimer, a polyols, or polyethylene glycol. The polymer is preferably branched to have a 2- or 3-dimensional structure. The polymer preferably comprises 5-50 or 5-100 binding molecules and 25-100 or 25-500 luminescent molecules.

The luminescent label useful for this invention has a molecular weight of <5,000, preferably <2,000, such as 500-2000 or 100-2000 Daltons. In one embodiment, the luminescent label is a fluorescent dye selected from the group consisting of: cyanine, coumarin, xanthene and a derivative thereof. For example, the fluorescent dye is Cy5 (molecule weight MW 792), Alexa Fluor 647, DyLight 350 (MW 874), DyLight 405 (MW793), DyLight 488 (MW 71011), DyLight 550 (MW 982), DyLight 594 (MW 1078), DyLight 633 (MW 1066), DyLight 650 (MW 1008), DyLight 680 (MW 950), DyLight 755 (MW 1092), DyLight 800 (MW 1050), an Oyster fluorescent dye, IRDye, or organic compounds comprising multiple rings chelated with a rare earth metal such as a lanthanide (Eu, Th, Sm, or Dy).

In another embodiment, the luminescent label is a chemiluminescent marker selected from the group consisting of: Ruthenium(II)tris-bipyridine (MW 1057), luminol (MW 177), acridinium ester (9[[4-[3-[(2,5-dioxo-1-pyrrolidinyl)oxy]-3-oxopropyl]phenoxy]carbonyl]-10-methyl-acridinium trifluoromethane sulfonate, MW 632), hemin (MW 652).

When the binding molecule is a polypeptide or protein, the luminescent label can covalently bind to it through a variety of moieties, including disulfide, hydroxyphenyl, amino, carboxyl, indole, or other functional groups, using conventional conjugation chemistry as described in the scientific and patent literature.

Covalent binding of a binding molecule to a polynucleotide can be effected through a variety of moieties, including aldehyde, ketone, isothiocyanate, imidate, inosine, acyl, and alkyl, using conventional conjugation chemistry, while derivatization with biotin is taught in many references. (Leary et al. (1983) Proc. Natl. Acad. Sci. USA 80:4045-4049; WO86/02929; EP063 879; Langer et al. (1981) Proc. Natl. Acad. Sci. USA 78:6633-6637; and EP2009 996).

In each step (b), (c), and (e), the reaction can be accelerated by agitating or mixing the solution in the vessel. For example, a lateral flow (orbital flow) of the solution across the probe tip can be induced, which accelerates the capture of target molecules by its binding partner immobilized to solid phase. For example, the reaction vessel can be mounted on an orbital shaker and the orbital shaker is rotated at a speed at least 50 rpm, preferably at least 200 rpm, more preferably at least 500 rpm, such as 500-1,000 rpm. Optionally, the probe tip can be moved up and down and perpendicular to the plane of the orbital flow, at a speed of 0.01 to 10 mm/second, in order to induce additional mixing of the solution above and below the probe tip.

In Step (f), the probe is washed 1-5 times, preferably 1-3 times in a wash vessel containing a wash solution. The wash solution typically contains buffer and a surfactant such as Tween 20.

Step (g) is cycling amplification by repeating steps (c)-(f) 1-10 times, preferably 1-5 times or 2-3 times. Each cycle consists of placing the probe back to the same reagent vessel, the same first wash vessel, the same amplification vessel, and the same second wash vessel.

Figure 1:
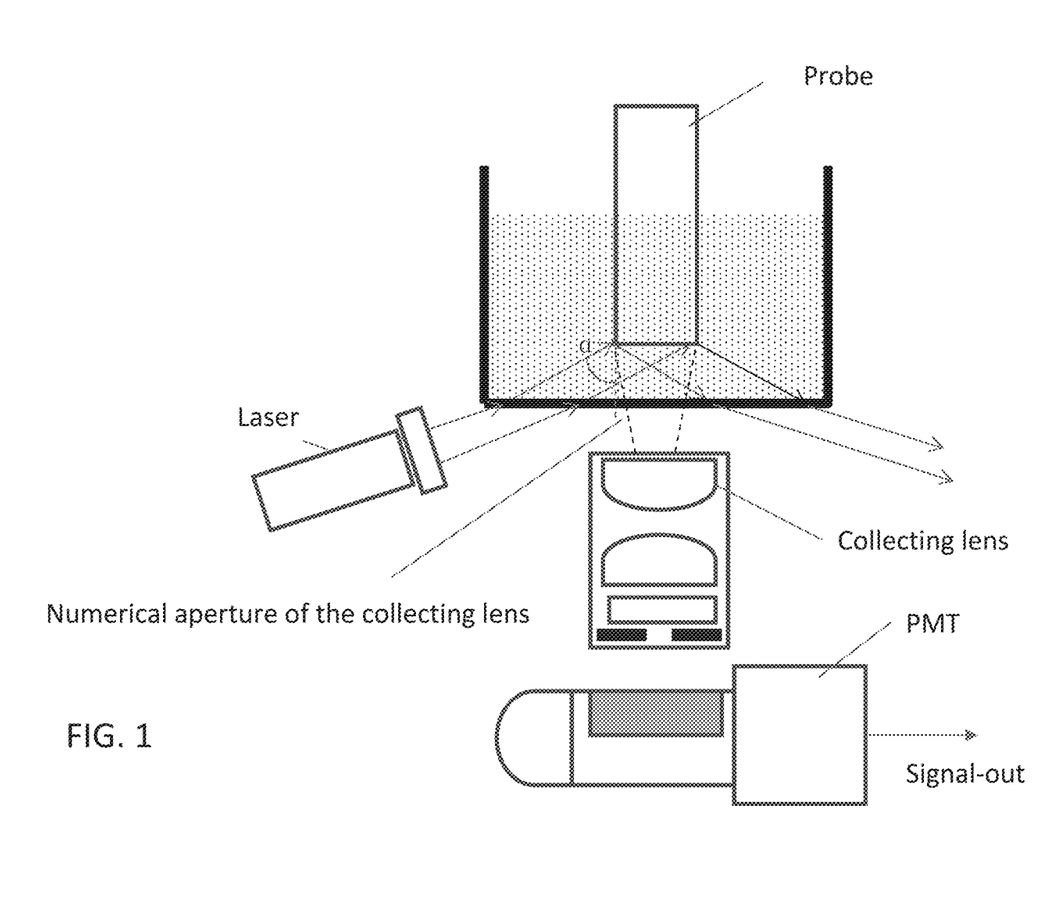
FIG. 1 illustrates an optical detecting system for detecting fluorescent signal from the sensing surface of the probe.

In Step (h), the immunocomplex is detected by reading the luminescent signal on the probe tip. For a fluorescent label, the probe is placed in a clear-bottom well and read by a detector, such as those described in US 2011/0312105 (FIG. 1).

For a chemiluminescent label, the probe is placed in a clear-bottom well containing a measurement solution having a co-reactant. For example, if the chemiluminescent label is Ruthenium(II)tris-bipyridine, the co-reactant is tripropylamine. If the chemiluminescent label is luminol, the co-reactants are hydrogen peroxide and a hydroxide salt in water. The light emitted is measured by a photomultiplier tube (PMT).

For electrochemiluminescence (ECL), the mechanism and the principal components of the ECL analyzer is described by Blackburn et al (Clin. Chem. 37: 1534-1539 (1991)), which is incorporated herein by reference. After the probe is placed in a clear-bottom well containing a measurement solution having a co-reactant, a voltage is applied to the working electrode and counter electrode, and the emitted light is measured by PMT.

Figure 2:
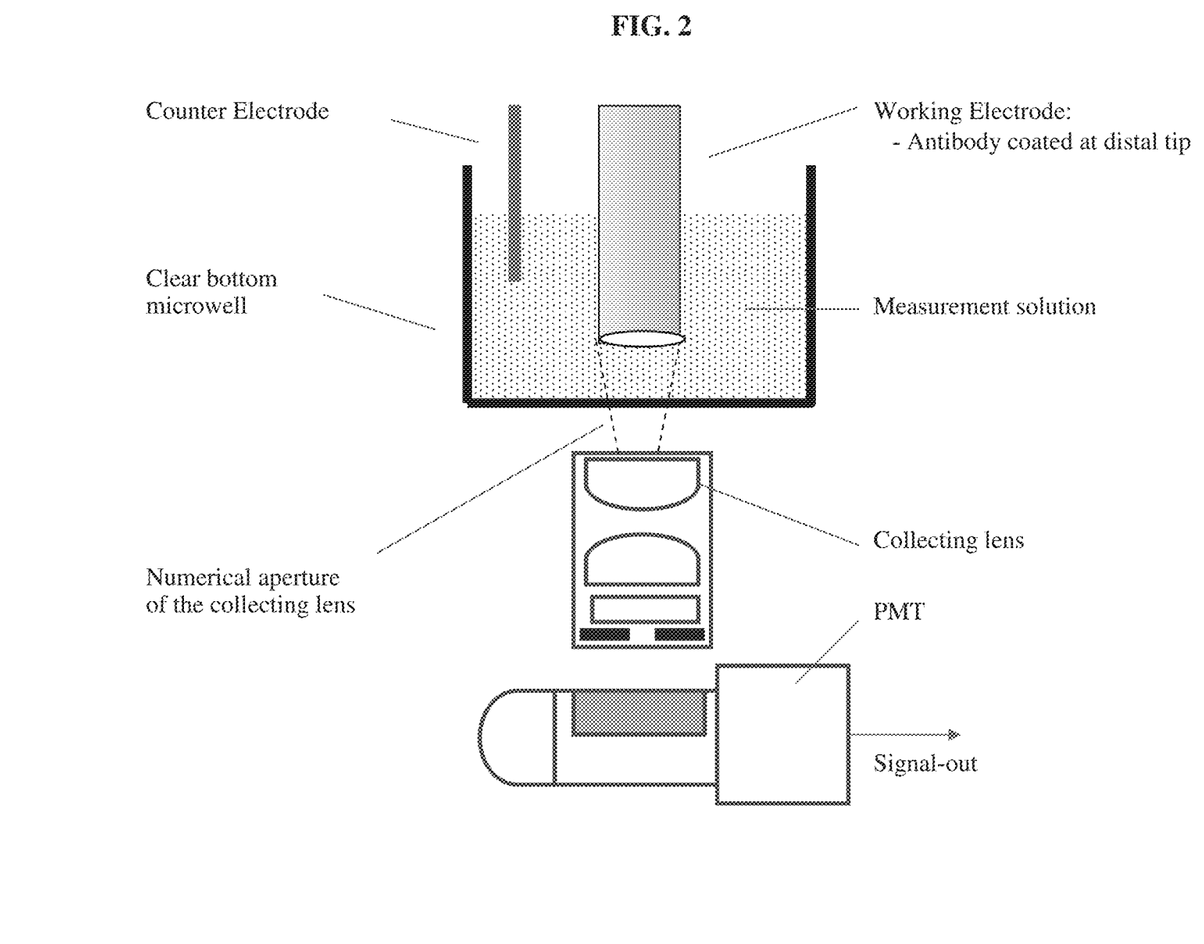
FIG. 2 illustrates an electrochemiluminescent detecting system for detecting chemiluminescent signal on the probe tip.

In a preferred embodiment, the antibody-coated probe serves as the working electrode of ECL analyzer (FIG. 2). This offers the advantage of efficient luminescence generation since the Ru(II)/tripropylamine red-ox reaction needs to occur at the electrode surface or very close proximity.

Figure 3:
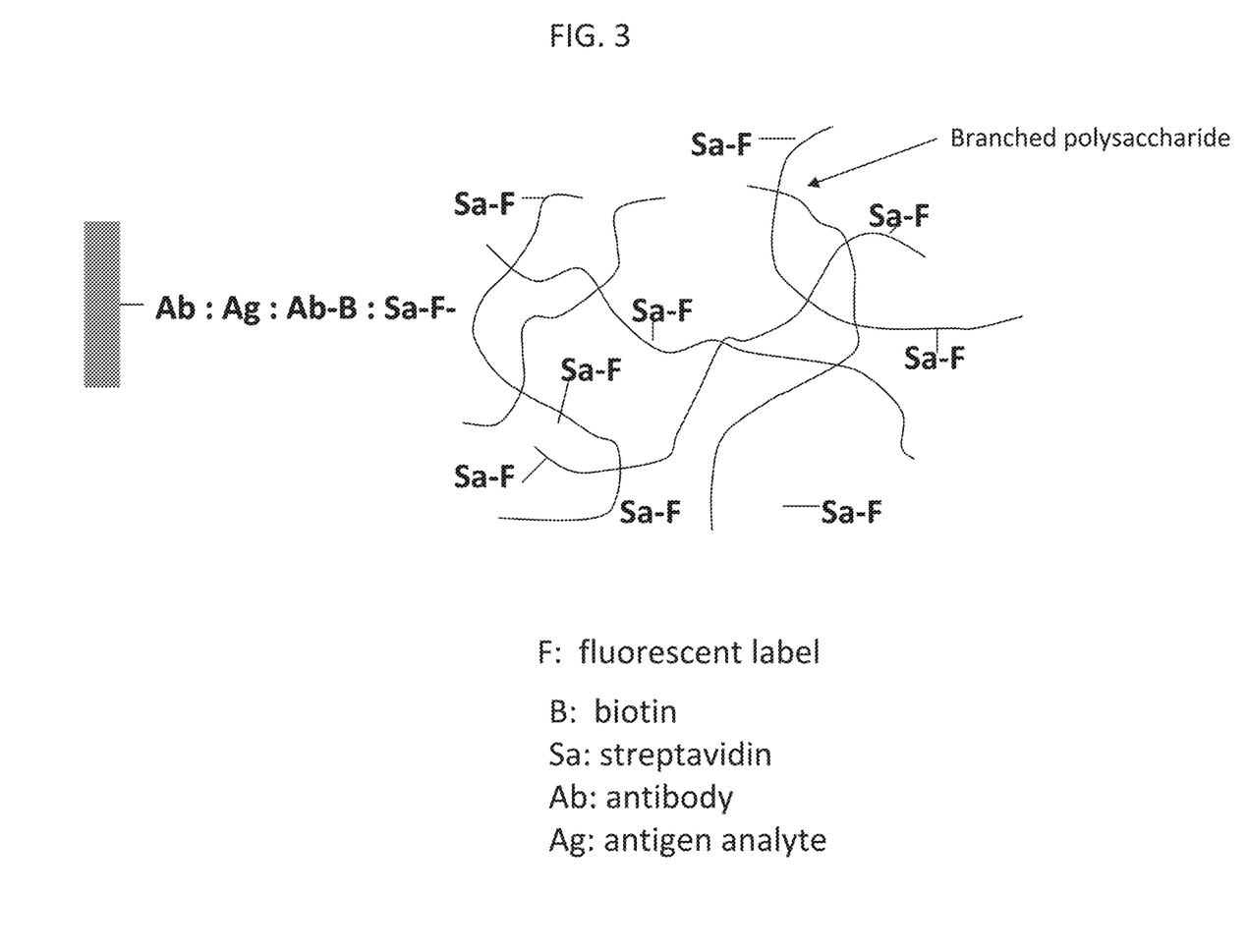
FIG. 3 illustrates an immunoassay format for detecting an antigen analyte. Ab: antibody, Ag: antigen, Sa: streptavidin, B: biotin, F: fluorescent label.
Figure 4:
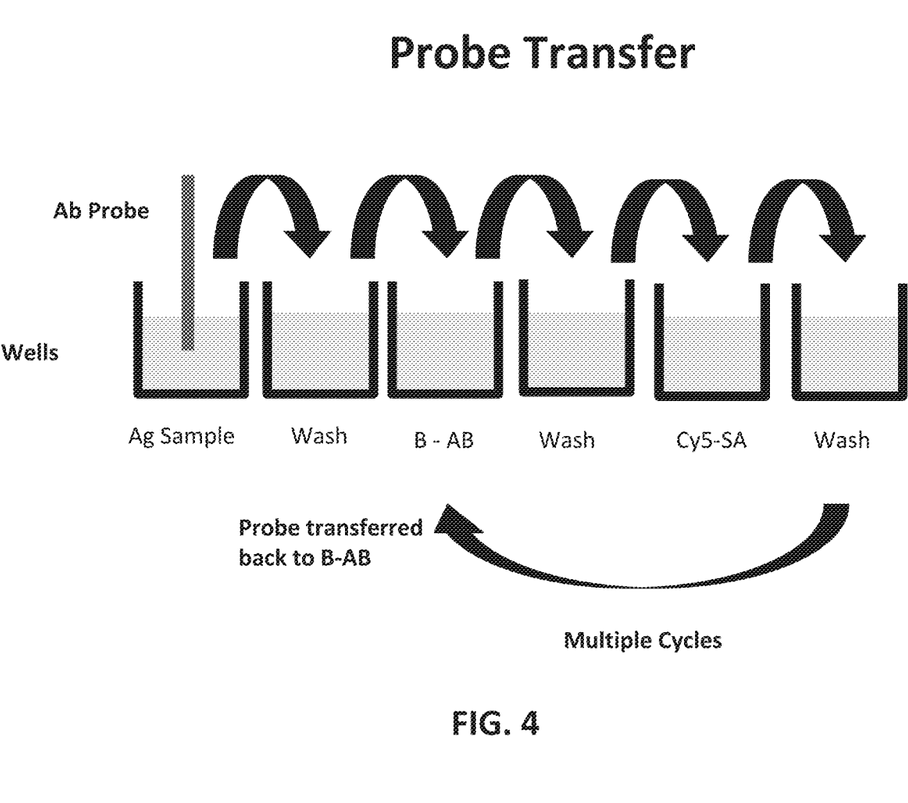
FIG. 4 illustrates probe transfer in cyclic amplification.

FIG. 3 illustrates one embodiment of an immunoassay format for detecting an antigen analyte. FIG. 4 illustrates the probe transfer in cyclic amplification.

There are several key features in the luminescent polymer that enable the cyclic amplification. The polymer itself should have low non-specific binding, should be greater than 400 or 500 kD in molecular weight to serve as an effective carrier of multiple binding molecules such as streptavidins. The ability to carry multiple binding molecules is important to enhance biotin binding capacity and to form alternating layers such as biotinylated antibody and streptavidin polymer. The polymer should be branched or crosslinked and have a two or three dimensional structure to further facilitate multiple layer formation. The size of the label is also a critical parameter. A high molecular weight label when conjugated to streptavidin is likely to alter its biotin binding capacity and present steric hindrance during multiple layer formation in cyclic amplification. The labels should be small, having molecule weights ≤5000 Daltons; preferably ≤2000 Daltons.

When the polymer conjugate binds to the first layer of biotin-antibody in the immune complex, it has sufficient residual biotin binding capacity to form another layer of biotin-antibody. The size of the polymer and its branched structure create an extended three dimensional complex on the probe surface that minimizes steric hindrance in the binding between the biotin-antibody and the polymer conjugate to form additional layers. The molecular weight of the polymer is large enough so that the labeled-streptavidin molecules are spaced apart. In a fluorescence assay, the space reduces energy transfer mediated fluorescent quenching. In an electrochemiluminescence assay, there is a similar advantage due to the spacing and structure of the polymer. The Ru(bpy) label bound in an immune complex on a solid phase reacts with tripropylamine (TPA) which is fluid phase. The Ru(bpy)/TPA decays emitting a photon regenerating the Ru(bpy) to react with another molecule of TPA. Eventually the TPA becomes depleted. If the Ru(bpy) label is densely packed on the surface, the TPA will become more quickly locally depleted. The crosslinked polymer yields more efficient chemiluminescence due to its spacing between the chemiluminescent label.

Negligible cyclic amplification with monomeric streptavidin labeled with Cy5 was observed. One would expect monomeric streptavidin with 4 binding sites and antibody labeled with 4-5 biotins could form alternating layers on the probe surface. However, probe surface where one member of the binding pair is already bound could limit its degree of rotation and sterically hinder a consequently layer formation. A second possibility for the Cy5-streptavidin's negative result is that there is layer formation but the Cy5 fluorescence is quenched. Cy5, as common with many fluorescent dyes, can have its fluorescence quenched, typically by a excitation energy transfer mechanism. The efficiency of energy transfer quenching is dependent on the distance between the donor and acceptor dyes. The formation of alternating layers can create densely packed Cy5-strepavidin where the Cy5 molecules are in close proximity and thus enabling quenching of fluorescence.

Another remarkable aspect of cyclic amplification is that the probe is transferred back and forth between the same reagent vessel, wash vessel, and amplification vessel, without having to use new vessels containing new solutions. The small surface area of the probe minimizes depletion of the reagent and the amplification polymer during the binding steps. This feature greatly simplifies the reagents required for the assay and overall consumable system designs. Each binding step in the cyclic amplification is only a short period of 30 seconds to 2 minutes, for example, one minute. Consequently, cyclic amplification does not caused pronged assay times. High sensitivity assays with times from 10-15 minutes are feasible.

High Molecular Weight Branched Polymer Containing Multiple Binding Molecules and Chemiluminescent Labels.

The present invention is also directed to a composition comprising (a) a branched polymer, having a molecular weight of at least 500,000 or 1 million Daltons, (b) at least 5 binding molecules, and (c) at least 25 chemiluminescent molecules, wherein the binding molecules and the chemiluminescent molecules are attached to the cross-linked FICOLL®. The composition preferably comprises 5-50 or 5-100 binding molecules and 25-100 or 25-500 chemiluminescent molecules.

The polymer can be a polysaccharide (e.g. FICOLL® or dextran), a polynucleotide, a dendrimer, a polyols, or polyethylene glycol. Polysaccharides in general exhibit negligible non specific binding to many of the solid phase materials commonly employed in immunoassays. FICOLL® is commercially available in 70K and 400K Dalton molecular weights. Crosslinked FICOLL® is a preferred polymer.

The chemiluminescent label useful for this invention has a molecular weight of <5,000, preferably <2,000, such as 500-2000 or 100-2000 Daltons. Preferred chemiluminescent molecules include, but are not limited to, ruthenium(II)tris-bipyridine, luminol, acridinium ester, and hemin.

In one embodiment, the chemiluminescent molecules are attached directly to the polymer. In another embodiment, the chemiluminescent molecules are attached indirectly to polymer through a binding pair.

Electrochemiluminescent Detection Device

The present invention is directed to an electrochemiluminescent detection system for measuring a chemiluminescent signal on a probe tip.

An electrochemiluminescent system comprising: (a) a probe having an aspect ratio of length to width at least 5 to 1, the probe having a first end and a second end, the second end having a sensing surface coated with an antibody and bound with an immunocomplex having a chemiluminescent label, wherein the probe is made of a conductive material and serves as a working electrode to produce an electrochemical reaction; (b) a counter electrode; (c) a collecting lens pointed toward the sensing surface; and (d) an optical detector for detecting the light emitted from the chemiluminescent label; wherein the collecting lens collects and directs the emitted light to the optical detector.

The probe can be constructed from any conductive material such as metals, metal oxides and carbon, e.g., silver, gold, platinum, copper, $TiO_2$, graphite, and any combination thereof. The probe can be any shape such as rod, cylindrical, round, square, triangle, etc., with an aspect ratio of length to width of at least 5 to 1, preferably 10 to 1. Because the probe is dipped in a sample solution and one or more assay solutions during an immunoassay, it is desirable to have a long probe with an aspect ratio of at least 5 to 1 to enable the probe tip's immersion into the solutions. The sensing surface of the probe is coated with analyte-binding molecules such as antibodies and bound with chemiluminescent labels.

In a preferred embodiment, the probe has a small tip for binding molecules. The tip has a smaller surface area with a diameter ≤5 mm, preferably ≤2 mm or ≤1 mm, e.g., 0.5-2 mm. The small surface of the probe tip provides several advantages. The present invention uses a probe that has a small tip for binding analytes. The tip has a smaller surface area with a diameter ≤5 mm, preferably ≤2 mm or ≤1 mm, e.g., 0.5-2 mm. The small surface of the probe tip provides several advantages such as low non-specific binding, small carry-over of the reagents, easy to wash, and small consumption of the reagents.

The photon of the emitted light is detected by photomultiplier tubes (PMT), silicon photodiode, or gold coated fiber-optic sensors.

FIG. 2 shows one embodiment of the invention. The lower end of the rod is used as a sensing surface. Chemiluminescent labels are bond to the sensing surface. To detect the luminescence, the rod's sensing end is immersed into a vessel with a clear bottom that contains a measurement solution containing a co-reactant. The clear bottom's material may be selected from plastic, glass or quartz. A ramp voltage is applied to the working electrode and the counter electrode, the emitted light is corrected by collecting lens and directed to PMT for measurement.

The unique aspect of the invention is that the probe serves as the working electrode, which offers the advantage of efficient luminescence generation since the Ru(II)/tripropylamine red-ox reaction needs to occur at the electrode surface or very close proximity. The optical device as configured is capable of applying a multitude of voltage waveforms at the working surface electrode with luminescence generally occurring around 1 volt.

The invention is illustrated further by the following examples that are not to be construed as limiting the invention in scope to the specific procedures described in them.

EXAMPLES

Example 1: Preparation of Probe Having Immobilized First Antibody

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (Biospacific), 10 µg/ml in PBS (phosphate-buffered saline) at pH 7.4. After allowing the antibody to adsorb to the probe for 20 minutes, the probe tip was washed in PBS.

Capture antibodies for troponin I (TnI) and brain naturetic peptide (BNP), obtained from HyTest, were labeled with fluorescein by standard methods. Typically, there were about 4 fluorescein substitutions per antibody. Anti-fluorescein coated probes were immersed in fluorescein labeled capture antibody solution, 5 µg/ml, for 5 minutes followed by washing in PBS.

Example 2: Preparation of Crosslinked FICOLL® 400-SPDP

Figure 5:
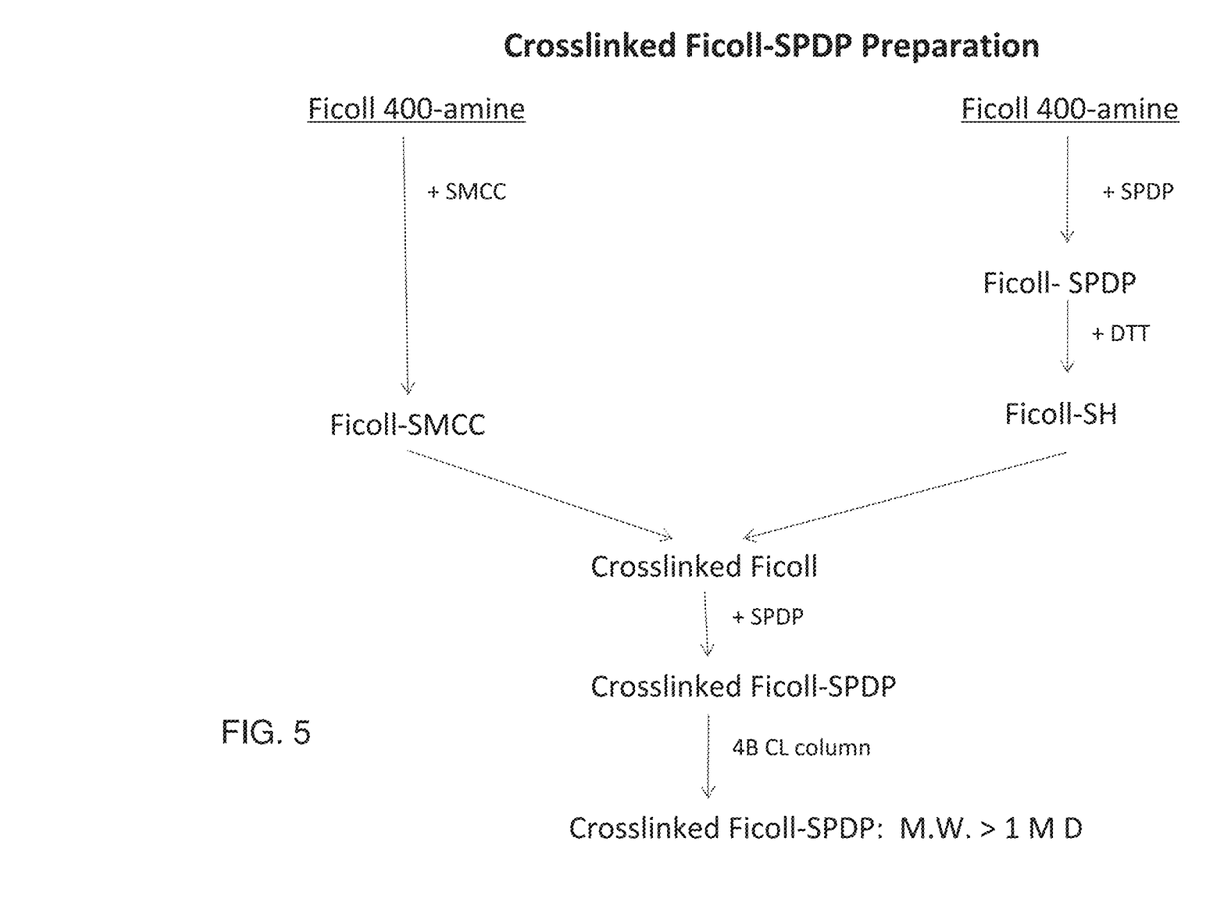
FIG. 5 shows a flow chart of the preparation crosslinked FICOLL® (copolymers of sucrose and epichlorohydrin) 400-SPDP.

Crosslinked FICOLL® 400-SPDP (succinimydyl 6-[3-[2-pyridyldithio]-proprionamido]hexanoate, Invitrogen) was prepared according to Example 1 of US 2001/0312105. FIG. 5 shows a flow chart of its preparation.

Example 3: Preparation of Cy5-Streptavidin

32 µL of Cy 5-NHS (GE Healthcare) at 5 mg/ml in DMF reacted with 1 ml of streptavidin (Scripps Labs) at 2.4 mg/ml in 0.1 M sodium carbonate buffer pH 9.5 for 40 minutes at 30° C. Applying the mixture to a PD 10 column (Pharmacia) removed unconjugated Cy 5. Spectral analysis indicated 2.8 Cy 5 linked per streptavidin molecule.

Example 4: Preparation of Cy5-Streptavidin-Crosslinked FICOLL®

5.8 µL of SMCC (succinimidyl 4-[N-malemidomethyl] cyclohexan-1-carboxylate) Pierce Chemical) at 10 mg/ml in DMF reacted with 2 mg Cy5-streptavidin (Example 2) in 1 ml PBS pH 7.4 for 1 hour at room temperature. Applying the mixture to a PD 10 column removed unbound SMCC.

The thiols on crosslinked FICOLL® 400-SPDP were deprotected by adding 30 µL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Cy5-streptavidin-SMCC was mixed with crosslinked FICOLL® 400-SH and reacted overnight at room temperature. 10 µL NEM (Aldrich) at 12.5 mg/ml was then added and reacted for ½ hour at room temperature. The conjugate was then purified on a Sepharose 4B CL column. It was estimated that the conjugate carried about 20 to 30 streptavidins per FICOLL® (2 million Daltons), and 2-3 Cy5s per streptavidin.

Example 5: Cy5-Streptavidin Vs. Cy5-Streptavidin-Crosslinked FICOLL® at $1^{st}$ Read (No Cycling)

A BNP assay was used to compare fluorescence signals of Cy5-Strepatavidin and Cy5-Streptavidin-Cx FICOLL®. The assay used a sandwich pair of BNP monoclonal antibodies, (Hytest). One was labeled with fluorescein and the second with biotin. Both labeling were done by standard methods with 4-5 haptens substituted per antibody. The fluorescein-antibody was bound to the probe as described in Example 1. For the assay, BNP calibrators (Hytest) were spiked into normal, pooled human plasma and then diluted 3 fold in PBS with 5 mg/ml BSA and 0.05% Tween 20 (assay buffer). The probe tip was immersed in the BNP samples and incubated for 5 minutes at room temperature with the sample wells subjected to orbital movement (1 mm diameter stroke) at 750 rpm. The probe was held stationary. The probe was washed 3 times for 10 seconds in PBS, 0.05% Tween 20. After the wash sequence, the probe was immersed in a solution containing biotinylated anti-BNP at 10 μg/ml in assay buffer, followed with a 2 min incubation at 500 rpm, then a 3× wash sequence. Probes were then transferred to solutions containing either Cy5-Strepavidin (Example 2) or Cy5-streptavidin-Cx FICOLL® (Example 3). The streptavidin in both cases was labeled with about 2-3 Cy5s and at a comparable concentration of 10 μg/ml. After one minute incubation at 500 rpm, the probes were taken through a wash sequence. Fluorescence at the distal tip of the probe was then measured in a optical configuration illustrated in FIG. 1. The assay configuration with the Cy5-streptavidin-Cx FICOLL® is diagramed in FIG. 4. The results are shown in Table 1. Measurements after the first binding are termed the first read (no cycling).

TABLE 1

First Read: Cy5-Streptavidin vs. Cy5-Streptavidin-Crosslinked FICOLL ®

| BNP, ng/ml | Cy5-SA Voltage | Cy5-SA-Cx FICOLL ® Voltage |
|---|---|---|
| 18 | 0.32 | 6.27 |
| 9 | 0.25 | 5.35 |
| 3 | 0.15 | 3.03 |
| 1 | 0.15 | 1.71 |
| 0.3 | 0.11 | 0.8 |
| 0.1 | 0.11 | 0.32 |
| 0 | 0.12 | 0.16 |

Data are mean of duplicate determinations

The results in Table 1 show that Cy5-streptavidin can only detect BNP above background about 9 to 18 ng/ml, while the FICOLL® conjugate can readily detect as low as 0.1 ng/ml. The results demonstrate that the high molecular weight FICOLL® polymer can serve to increase sensitivity.

Example 6: Cyclic Amplification

At the end of the 1$^{st}$ read, the probes of Example 5 were carried out further amplification cycles. A cycle consists of placing probes back in the same biotin-antibody solution for 1 min at 500 rpm, followed a wash sequence, then back in the streptavidin solution for one minute at 500 rpm followed by a wash sequence. The cycles are intended to build up alternating layers of biotin-antibody and streptavidin. FIG. 5 depicts the transfer of the probe from well to well during the cyclic amplification process. At the end of each amplification cycle, fluorescence at the probe tip is measured.

Table 2 shows a continuation of the BNP assay from Table 1, where the probes underwent two amplification cycles, Cycle 1 and Cycle 2.

TABLE 2

Cycling Amplifications: Cy5-Streptavidin vs. Cy5-Steptavidin-Crosslinked FICOLL ®

| BNP ng/ml | Cy5-SA | | | Cy5-SA-Cx FICOLL ® | | |
|---|---|---|---|---|---|---|
| | 1st Read | Cycle 1 | Cycle 2 | 1st Read | Cycle 1 | Cycle 2 |
| 18 | 0.32 | 0.38 | 0.41 | 6.27 | 8.36 | 10.92 |
| 9 | 0.25 | 0.27 | 0.28 | 5.35 | 7.78 | 10.49 |
| 3 | 0.15 | 0.21 | 0.22 | 3.03 | 4.77 | 7.01 |
| 1 | 0.5 | 0.15 | 0.16 | 1.71 | 2.77 | 4.41 |
| 0.3 | 0.11 | 0.11 | 0.11 | 0.8 | 1.37 | 2.19 |
| 0.1 | 0.11 | 0.11 | 0.12 | 0.32 | 0.53 | 0.82 |
| 0 | 0.12 | 0.12 | 0.13 | 0.16 | 0.25 | 0.36 |

Data are mean of duplicate determinations

The results of Table 2 indicate that the Cy5-streptavidin does not have significant increase in signal through 2 cyclic amplification cycles. On the contrary, the Cy5-streptavidin-crosslinked FICOLL® conjugate shows about a doubling of fluorescence signal after two cycles beyond the initial binding (1st Read). These results indicate that achieving cyclic amplification with alternating layers of biotin-antibody and Cy5-streptavidin is not a matter solely depending transferring the probe back and forth between the two reagents. Cyclic amplification can only be achieved with the Cy5-streptavidin-crosslinked FICOLL® conjugate.

Example 7: BNP Assay with Cyclic Amplification

Table 3 contains results of a BNP assay, performed with the same protocol as in Example 5, with more cycling amplification steps.

TABLE 3

BNP Assay with Multiple Cycling Amplification Steps

| BNP, pg/ml | 1st Read | Cycle 1 | Cycle 2 | Cycle 3 | Cycle 4 |
|---|---|---|---|---|---|
| 580 | 1.13 | 3.11 | 6.37 | 11.49 | PMT sat. |
| 58 | 0.18 | 0.42 | 0.82 | 1.51 | 2.57 |
| 14 | 0.13 | 0.29 | 0.58 | 1.06 | 1.81 |
| 0 | 0.15 | 0.23 | 0.42 | 0.75 | 1.27 |

Data are mean of duplicate determination

The results of Table 3 indicate that the cycling amplification boosts sensitivity in immunoassays. In this example, the signal of 14 pg/ml BNP sample is comparable to that of the negative sample at the first read. After the 2nd cycle amplification, the 14 pg/ml is readily resolved. The assay performed 4 amplification cycles and the fluorescence signals steadily increased after each cycle.

As many as 9 amplification cycles have been performed in other experiments and the fluorescence signals still steadily increased after each cycle.

Example 8: TnI Assay with Cyclic Amplification

Table 4 presents data from a troponin I (TnI) assay using the cyclic amplification method. A sandwich pair of monoclonal antibodies (Hytest) was used, one of which was labeled with fluorescein and the second with biotin. The hapten labeling were by standard methods. Probe coating with the fluorescein-anti-TnI was as described in Example 1. The anti-TnI coated probe was immersed in TnI samples diluted 3 fold in assay buffer and incubated at room temperature for 20 minutes with samples wells subjected to orbital flow of 750 rpm. After a wash sequence, the probes were immersed in a solution of B-anti-TniI at 10 μg/ml for 2 minutes at 500 rpm, followed by incubation in the Cy5-

SA-FICOLL® reagent for 1 minute with 500 rpm flow. Two subsequent amplification cycles were performed by cycling the probe back into the B-anti-TnI solution (1 min incubation) thru wash sequence to Cy5-SA-FICOLL® (1 minute incubation) followed by a wash sequence. All steps were performed at room temperature with 500 rpm flow. At the completion of each amplification cycle, fluorescence of the probe tip was measured and the results are shown in Table 4.

TABLE 4

Troponin I Assay with Cycling Amplification Steps

| TnI, pg/ml | 1st Read | Cycle 1 | Cycle 2 |
|---|---|---|---|
| 1000 | 2.34 | 7.06 | 13.41 |
| 100 | 0.54 | 1.43 | 3.17 |
| 10 | 0.31 | 0.66 | 1.43 |
| 0 | 0.31 | 0.53 | 1.04 |

Note:
Data mean of duplicate determinations

Data depicted in Table 4 shows that cyclic amplification method boosts sensitivity. The 10 pg/ml TnI sample, which at the first read is undetected, has its fluorescence greater than the negative sample after 2 cycles of amplification.

Example 9: Assay Precision with Cyclic Amplification

One would expect that with the formation of multiple layers of high molecular weight complexes that imprecision would increase with more amplification steps. However, Table 5 illustrates another unexpected aspect of the cyclic amplification method.

A precision study was performed using clinically relevant BNP levels following the protocol described in Example 5. The % CV (coefficient of variation) for BNP concentration units (pg/ml) are shown in Table 5. The results show that the cycling amplification method has high precision with a C.V. of <10%.

TABLE 5

BNP Assay Precision

| BNP | 100 pg/ml | 500 pg/ml | 1500 pg/ml |
|---|---|---|---|
| 1st Read | 17.3% CV | 2.2% CV | 4.4% CV |
| Cycle 1 | 8.1% CV | 2.5% CV | 4.6% CV |
| Cycle 2 | 7.4% CV | 2.8% CV | 5.5% CV |
|  | n = 8 | n = 8 | n = 8 |

Example 10: Reduction in Minimum Detection Limit

Table 6 shows results of BNP assays performed with three cycling amplification steps using protocols described in Examples 4 & 5. Results of a BNP calibration curve and the mean, standard deviation, and two standard deviations of 16 replicates of a negative sample are in Table 6. The high end of the BNP appears to start saturating the probe at around 3 to 6 ng/ml and the assay has sensitivity down to the low pg/ml range. 2 standard deviations is a common means of determining the minimum detection limit of an immunoassay. Data in Table 6 show that the minimum detection limit progressively decreases from 6.4 pg/ml at first read to 1 pg/ml after 3 cycling amplification. At first read, the S.D. of the negative sample is 0.0078 V, where the major source of variation is the particular instrument employed in the assay. Instrument Variation is about ±0.007V. With cyclic amplification, the sensitivity is improved by increasing the immuno-specific signal while the instrument measurement noise remains constant.

TABLE 6

Minimum Detection Limit Improvement with Cyclic Amplification.

| | PMT Voltage | | | | | | | |
|---|---|---|---|---|---|---|---|---|
| BNP (pg/ml): | 6000 | 3000 | 1000 | 333 | 111 | 37 | 12 | 0 |
| 1st Read | 9.48 | 7.87 | 4.3 | 2.32 | 0.83 | 0.29 | 0.07 | 0.04 |
| Cycle 1 | 11.62 | 10.14 | 6.7 | 4.53 | 1.8 | 0.66 | 0.16 | 0.06 |
| Cycle 2 | Sat. | 12.37 | 8.73 | 6.94 | 3.2 | 1.22 | 0.29 | 0.09 |
| Cycle 3 | Sat. | Sat. | 10.6 | 9.14 | 4.91 | 2.01 | 0.45 | 0.13 |

| | S.D.* | | Detection Limit |
|---|---|---|---|---|
| | Neg. | (n = 16) | 2× S.D. | (pg/ml) |
| 1st Read | 0.04 | 0.0079 | 0.016 | 6.4 |
| Cycle 1 | 0.06 | 0.012 | 0.024 | 3.7 |
| Cycle 2 | 0.09 | 0.015 | 0.03 | 2.4 |
| Cycle 3 | 0.13 | 0.016 | 0.032 | 1.1 |

Example 11: Preparation of Streptavidin-Crosslinked FICOLL® with Chemiluminescent Labels 0.176 µg of Ruthenium(II)tris-bipyridine-NHS (MesoScale Discovery, R91BN-2) in 35 µl dimthylformaide is mixed with 1 mg streptavidin in PBS pH 7.4 and allowed to react for one hour at room temperature. Typically about 2 to 4 Ru labels are linked per streptavidin molecule. The resulting Ru-streptavidin conjugate is purified on a PD-10 column (Pharmacia). 2.9 µL of SMCC (Pierce Chemical) at 10 mg/ml in DMF reacted with 1 mg of Ru-streptavidin in 1 ml PBS pH 7.4 for 1 hour at room temperature. The mixture is applied to a PD 10 column to remove unbound SMCC.

The thiols on crosslinked FICOLL® 400-SPDP are deprotected by adding 30 µL DTT at 38 mg/ml to 1 mg crosslinked FICOLL® 400-SPDP in 1 ml PBS and reacting for 1 hour at room temperature followed by a PD 10 column to purify the crosslinked FICOLL®.

The Ru-streptavidin-SMCC is mixed with crosslinked FICOLL® 400-SH and reacted overnight at room temperature. 10 µL NEM (Aldrich) at 12.5 mg/ml is then added and reacted for ½ hour at room temperature. The conjugate is then purified on a Sepharose 4B CL column. The resulting conjugate has about 20 streptavidins per crosslinked FICOLL® and 2-4 Ru per streptavidin.

Example 12: Cyclic Amplification with Chemiluminescent Labels 1 mm diameter anti-BNP coated probe, prepared as described in Example 1, is immersed in the BNP samples and incubated for 5 minutes at room temperature with the sample wells subjected to orbital movement (1 mm diameter stroke) at 750 rpm. The probe was held stationary. The probe is washed 3 times for 10 seconds in PBS, 0.05% Tween 20. After the wash sequence, the probe is immersed in a solution containing biotinylated anti-BNP at 10 µg/ml in assay buffer, followed with a 2 minute incubation at 500 rpm, then a 3× wash sequence. The probe is then transferred to solutions containing Ru-streptavidin-Cx FICOLL® at a concentration of 10 µg/ml. After 1 minute incubation at 500 rpm, the probes are taken through a wash sequence, then undergo 2 amplification cycles. A cycle consists of placing probes back in the same biotin-antibody solution for 1 min at 500 rpm, followed a wash sequence, then back in the streptavidin solution for one minute at 500 rpm, and followed by a wash sequence. At the completion of the last wash step, the probe is immersed in a clear bottom microwell containing the measurement solution with the co-reactant, tripropylamine (MesoScale Discovery, Read Buffer S, R925C-3), and read by the optical device of FIG. 2.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. An electrochemiluminescent system comprising: (a) a probe having an aspect ratio of length to width of at least 5 to 1, the probe having a first end and a second end, the second end having a sensing surface coated with an antibody and bound with immunocomplexes having chemiluminescent labels, wherein the probe is made of a conductive material and serves as a working electrode to produce an electrochemical reaction at the electrode surface; (b) a sample vessel, reagent vessels, and wash vessels, wherein the probe is not attached to any of the vessels and the probe is configured to be transferrable among the vessels during an immunoassay; (c) a counter electrode; (d) a collecting lens pointed toward the sensing surface; and (e) an optical detector for detecting the light emitted from the chemiluminescent labels; wherein the collecting lens collects and directs the emitted light to the optical detector.

2. The electrochemiluminescent system according to claim 1, wherein the diameter of the sensing surface is ≤5 mm.

3. The electrochemiluminescent system according to claim 1, wherein the diameter of the sensing surface is ≤2 mm.

4. The electrochemiluminescent system according to claim 1, wherein the probe is made of a conductive material selected from the group consisting of metals, metal oxides and carbon.

5. The electrochemiluminescent system according to claim 4, wherein the probe is made of silver, gold, platinum, copper, $TiO_2$, graphite, or any combination thereof.

6. The electrochemiluminescent system according to claim 1, wherein the probe has an aspect ratio of length to width at least 10:1.

7. The electrochemiluminescent system according to claim 1, further comprising a clear bottom vessel containing a solution and a co-reactant for dipping the probe and the counter electrode during measurement of luminescence.

* * * * *